United States Patent [19]

Broussard et al.

[11] Patent Number: 4,863,971

[45] Date of Patent: Sep. 5, 1989

[54] SYNTHESIS GAS CONVERSION WITH PEROVSKITE CATALYSTS

[75] Inventors: Jerry A. Broussard, Summit, N.J.; Leslie E. Wade, Corpus Christi, Tex.

[73] Assignee: Hoechst Celanese Corporation, Somerville, N.J.

[21] Appl. No.: 28,257

[22] Filed: Mar. 20, 1987

[51] Int. Cl.$^4$ .............................................. C07L 27/06
[52] U.S. Cl. ................................... 518/713; 518/715; 518/716; 518/721
[58] Field of Search ................. 518/713, 715, 716, 721

[56] References Cited

U.S. PATENT DOCUMENTS

| | | | |
|---|---|---|---|
| 3,972,837 | 8/1976 | Acres et al. | 518/715 X |
| 4,089,810 | 5/1978 | Diwell et al. | 518/715 X |
| 4,126,580 | 11/1978 | Lauder | 518/715 X |
| 4,312,955 | 1/1982 | Bartley | 518/713 |

OTHER PUBLICATIONS

Watson et al., J of Catalysis, 74, 282-295, 1982.

*Primary Examiner*—Howard T. Mars
*Attorney, Agent, or Firm*—Lynch, Cox, Gilman & Mahan

[57] ABSTRACT

A process for synthesis gas conversion utilizing perovskite catalysts is disclosed herein. The perovskites utilized in the process have a carbon selectivity of about eight mol percent or more for oxygenated compounds containing one to six carbon atoms. The process comprises reacting synthesis gas in the presence of a perovskite catalyst in the temperature range of about 200° C. to about 400° C.

36 Claims, 1 Drawing Sheet

SYNTHESIS GAS CONVERSION WITH PEROVSKITE CATALYSTS

BACKGROUND OF INVENTION

1. Field of Invention

This invention relates to mixed metal oxides with the perovskite structure and their use as catalysts. More particularly, this invention relates to the use of perovskites as catalysts for the conversion of synthesis gas (syn gas).

2. Prior Art

The conversion of syn gas, which is comprised primarily of carbon monoxide and hydrogen, to various carbon containing compounds is well known. A variety of catalysts, including particularly the group 8 and group 1B and 2B metals have been employed in the conversion of syn gas. Most of these catalysts have mainly resulted in the formation of broad, complex mixtures of hydrocarbons and oxygenated organic compounds and carbon dioxide. Hydrocarbon formation, particularly methane formation, is thermodynamically favored over the formation of oxygenated organic compounds. In addition, the formation of carbon dioxide and hydrogen is also favored over the formation of oxygenated organic compounds, particularly those containing two or more carbon atoms. Therefore, in the conversion of syn gas to useful organic products, there is a need for catalysts that selectively produce lower oxygenated organic compounds, particularly those containing one to six carbon atoms from syn gas.

In U.S. Pat. No. 4,312,955, lanthanum rhodate perovskites are used as catalysts for the highly selective conversion of syn gas to methanol. Some of the perovskites produce other oxygenated compounds, such as ethanol and propanol. However, non-lanthanum rhodate catalysts are not disclosed.

In "The Formation of Oxygen-containing Organic Molecules by the Hydrogenation of Carbon Monoxide using a Lanthanum Rhodate Catalyst," by Watson and Somorjai, *Journal of Catalysis* 74, 282-295, 1982, syn gas conversion employing $LaRhO_3$ at a reaction temperature of 225° C.-375° C. and at a pressure of 1 to 10 atmospheres is disclosed. At lower temperatures, the major product observed is methanol, but at 300° C. the major products are acetaldehyde and ethanol. The combined selectivity of this catalyst for acetaldehyde and ethanol is reported to be 45-49 percent. However, other perovskite catalysts are not disclosed.

In U.S. Pat. No. 4,126,580 a variety of perovskite catalysts is disclosed. According to the patent, the perovskite catalysts, and particularly those containing Fe, Co, Ni or Ru, can be utilized in the reduction of carbon monoxide with hydrogen at temperatures ranging from 150° C.-600° C. and pressures up to 15,000 psi to produce hydrocarbons with or without the concomitant formation of alcohols, aldehydes, ketones or fatty acids. However, there is no disclosure that any of the catalysts can selectively produce oxygenated compounds.

U.S. Pat. No. 2,517,035 discloses the use of $La_2O_3$ as a promoter for cobalt and iron catalysts in syn gas conversion. According to the patent, the preferred catalyst is a mixture of $Co_3O_4$, diatomaceous earth, and magnesium oxide. However, no disclosure is made of the catalytic activity of perovskites.

It is an object of this invention to provide a means for producing lower oxygenated organic compounds from synthesis gas.

It is a further object of this invention to provide a means for selectively producing lower oxygenated organic compounds from synthesis gas utilizing perovskite catalysts.

It is also an object of this invention to form high yields of lower oxygenated organic compounds, particularly those containing one to six carbon atoms from synthesis gas.

These and other objects are obtained by the process or products of the present invention.

SUMMARY OF INVENTION

The process of this invention comprises converting syn gas to hydrocarbons and oxygenated organic compounds utilizing a perovskite catalyst at a temperature in the range of about 200° C. to 400° C. The process finds particular utility in the selective production of lower oxygenated organic compounds such as methanol, ethanol, acetaldehyde, acetic acid, esters of acetic acid, propanols, propionic acid, esters of propionic acid, butanols, pentanols, and hexanols.

DETAILED DESCRIPTION OF INVENTION

Figure 1:
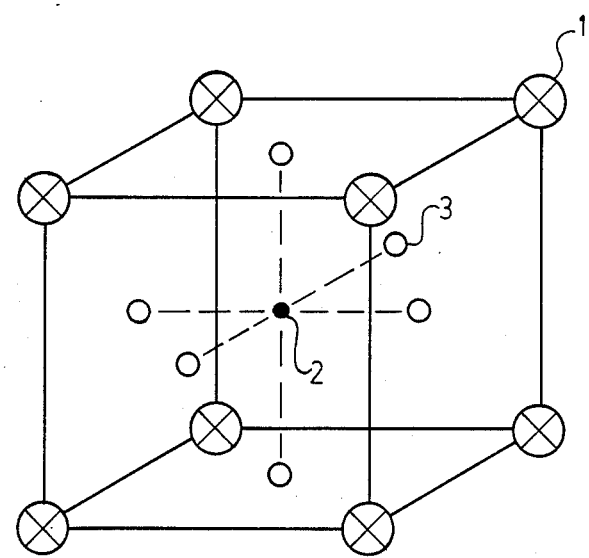

Perovskites are a well known class of compounds. They are crystalline, mixed metal oxides having the general empirical formula $ABO_3$ and containing substantially equal numbers of metal cations at the A and B sites in the perovskite crystal lattice structure. The crystal structure is usually cubic or distorted cubic and can be represented in FIG. 1, wherein 1 represents an A site cation, 2 represents a B site cation, and 3 represents an oxygen atom. At the center of the cubic structure is the smaller B site cation which is coordinated with six oxygen atoms. The faces of the cubes are occupied by oxygen atoms. Variation and distortion of the cubic crystal structure occurs among perovskites. Some of the distortions include rhombohedral, orthorhombic, psuedocubic, tetragonal, and pseudo-tetragonal configurations.

Virtually all the metals of the periodic table, including main group metals, transition metals, lanthanides, and actinides have been incorporated into various perovskite structures. More specifically, the A site metals of simple ternary perovskites ($ABO_3$) usually are derived from the periodic table groups 1A, 1B, 2A, 2B, 3B, 4A, and 5A, lanthanide rare earth metals, (atomic numbers 58-71), and the actinide rare earth metals (atomic numbers 90-104). The particularly preferred perovskite compositions utilize A site metals that are either La, Ba, or Nd. The B site cations are usually from the periodic table groups 1B, 2B, 3A, 4A, 4B, 5B, 6B, 7B and 8. The preferred B site metals are Ti, Mn, Fe, Co, Ni, Cu, Ru, Rh, Ir, and Pt. (The convention used for defining the A and B groups of the periodic table is that of the *CRC Handbook of Chemistry and Physics,* 58th Edition, R. C. Weast, Ed., Chemical Rubber Press, Inc.: Cleveland, 1977.)

It is possible to carry out a wide range of isomorphous substitutions in the perovskite structure. Consequently, perovskites with the empirical formula $A_xA'_{(1-x)}B_yB'_{(1-y)}O_3$ can be made where x and y are between 0 and 1, and A, A', B, and B' are all different metal cations. For example, in $La_{1.0}Ni_{0.5}Co_{0.5}O_{3.0}$, $x=1$, $y=0.5$, A=La, B=Ni, and B'=Co. Isomorphous substitutions allow the structural and electronic properties of perovskite catalysts to be modified to improve selectivity for oxygenated organics.

The preferred perovskites have a selectivity for producing lower oxygenated organic compounds, particularly those containing one to six carbon atoms above the eight mol percent level, i.e. wherein the percent is expressed as the moles of carbon contained in the lower oxygenated organic products as a percent of the total moles of carbon contained in the reaction products.

As used herein, the term "lower oxygenated organic compounds" refers to organic compounds containing carbon, hydrogen, and oxygen atoms. It does not refer to hydrocarbons, water or carbon dioxide which are all potential products of syn gas conversion. Examples of lower oxygenated organic compounds include methanol, ethanol, acetaldehyde, acetic acid, esters of acetic acid, propanols, propionic acid, esters of propionic acid, butanols, pentanols, and hexanols.

The preferred perovskites having the desired selectivities to lower oxygenated organic compounds are as follows: $LaMO_3$ where M=Co, Ni or Fe; $LaNi_{0.5}Fe_{0.5}O_3$; $LaNi_{0.5}Co_{0.5}O_3$; $LaFe_{0.5}Co_{0.5}O_3$; $LaMn_{0.5}Ni_{0.5}O_3$; $LaMn_{0.5}Fe_{0.5}O_3$; $LaFe_{0.5}Ru_{0.5}O_3$; $LaFe_{0.5}Ti_{0.5}O_3$; $LaNi_{0.5}Ru_{0.5}O_3$; $LaCu_{0.5}Ti_{0.5}O_3$; $LaCu_{0.5}Mn_{0.5}O_3$; amorphous or crystalline $BaMO_3$ where M=Ru, Rh, or Pt; amorphous $BaIrO_3$; and $NdNiO_3$.

The preparation of perovskites is well known in the art. Procedures for preparing perovskite compounds are disclosed in *Structure, Properties and Preparation of Perovskite Type Compounds* by Francis Galasso, Pergamon Press, Oxford 1969 and U.S. Pat. Nos. 4,126,580 and 4,312,955 which are incorporated herein by reference.

Perovskite catalysts can also be prepared by coprecipitation and calcination at elevated temperatures. The appropriate metal nitrates or metal chlorides are precipitated as mixed hydroxides with tetramethyl ammonium hydroxide. For example, when $LaCoO_3$ is prepared, the appropriate metal nitrates are $La(NO_3)_3 \cdot 6H_2O$ and $Co(NO_3)_2 \cdot 6H_2O$. In order to prepare these materials, equimolar amounts of the appropriate metal salts are dissolved in distilled water, and the solution is placed into an addition funnel. The metal salt solution is added dropwise to an aqueous solution of tetramethyl ammonium hydroxide over about 30-40 minutes. Generally, a 200 percent excess of tetramethyl ammonium hydroxide is used to convert the soluble metal salts to insoluble metal hydroxides. For example, where 0.05 mole of each metal salt is dissolved in water, about 0.75 mole of tetramethyl ammonium hydroxide is used.

The precipitate that results from the addition of the metal salts to the tetramethyl ammonium hydroxide is stirred for several hours, preferably two to three hours, and then suction filtered. The resulting filter cake is washed repeatedly with distilled water and suction filtered as dry as possible after each washing. The washings continue until the pH of the washings is in the range of about eight to nine. The resulting precipitate is dried in a vacuum oven at about 150° C. and at a pressure of about 350 mm of Hg, absolute. Air can be swept through the oven to facilitate the evaporation of the water. After the precipitate is dried, it is ground into a powder, preferably to a particle size of ten mesh or smaller.

Next, the powder is placed in a crucible and heated in a calcining oven equipped with a means for permitting air or oxygen to be swept through the heating chamber. The calcining temperature is usually in the range of about 350° C. to about 1100° C. but can reach as high as 1500° C. The heating times and temperatures required for the formation of perovskite compounds will depend upon the particular composition being formed. Generally, the required heating times are shorter at higher temperatures. The sample is usually heated at a temperature of 700° C. overnight. After, calcination, the sample is ground to an appropriate mesh, such as less than 50 mesh, before being used as a catalyst in syn gas conversion.

The ground perovskite may be used as is as a catalyst in syn gas conversion. However, the powdered catalyst has a tendency to be blown out of the reaction vessel when syn gas is passed over the catalyst. Consequently, it is preferred to mix the perovskite powder with a binder to prevent the catalyst from being entrained by the syn gas and carried out of the reactor. The binder must be inert under reaction conditions. An example of a suitable binder is silicon dioxide. Silicon dioxide is catalytically inactive for syn gas conversion, and the ratio of silicon dioxide to perovskite catalyst has a negligible effect on the selectivity of the catalyst for oxygenated organic compounds.

Generally, it is preferred to mix the perovskite with silicon dioxide at a weight ratio of between 1:1 to 1:5, respectively. Usually, either a 1:1 or a 1:4 ratio is employed. The silicon dioxide is usually at about a 50-400 mesh powder and preferably about a 100 to about 200 mesh powder. The silicon dioxide and perovskite powder are mixed together and pressed into a tablet using any suitable means known to those skilled in the art. For example, a ram and die (diameter=one inch) is charged with an intimate mixture of perovskite powder and silicon dioxide powder. The ram and die assembly is placed in a hydraulic press and compressed to a total pressure of about 20,000-25,000 pounds and held at that pressure for about 5-20 minutes. The resulting tablet is then removed from the ram and die, crushed and sieved to a suitable size, preferably ten to forty mesh, prior to being used as a catalyst for syn gas conversion.

The preparation of syn gas is well known in the art. Syn gas can be produced in a variety of ways and from a variety of materials, such as coal or natural gas. Syn gas can be converted to oxygenated organic compounds in any suitable container or reactor which permits the reactant gases to be brought in contact with the catalyst surface at pressures above one atmosphere, absolute, and temperatures above about 200° C. The reactor should be equipped with the following:

1. Lines to introduce syn gas feed to the reactor and remove products from the reactor;
2. A device for heating the reactor;
3. A temperature sensor and controller for detecting and controlling the temperature of the reactor in the temperature range of about 200°-400° C.;
4. Flow controllers to control the rate of syn gas feed to the reactor; and
5. A pressure controller to control the reactor pressure in the range of about 100-20,000 pounds per square inch (psi), and preferably about 100-5000 psi.

A suitable reactor is a standard U-tube reactor with a catalyst bed volume of about 30-40 millimeters. It is well known in the art that the degree of selectivity for oxygenated compounds can be affected by the geometry of the reactor. Since the conversion of syn gas is an exothermic reaction, it is necessary for the reactor to permit heat to be dissipated readily. If heat is not dissipated, the temperature within the reactor will become elevated and thereby affect what products result. Generally, higher temperatures within the reactor favor hydrocarbon formation.

The syn gas that is fed into the reactor can have a ratio of about 1:20 to about 20:1 by volume of hydrogen to carbon monoxide, preferably a ratio of about 1:2 to 5:1, and most preferably about a 2:1 ratio.

The reaction pressure can be from about 100 psig to about 20,000 psig, preferably about 500 to 10,000 psig, and most preferably about 970 to about 1030 psig.

The gas hourly space velocity is generally in the range of about 1,000 to 100,000 liters of reactant gases per liter of catalyst charged to the reactor per hour at 25° C. and one atmosphere of pressure, preferably about 2000 to about 50,000, and preferably about 2350 to about 4,000.

It is preferred to keep the syn gas conversion temperature below about 400° C. At temperatures much above 400° C., the crystal lattice structure of the perovskite catalyst may be destroyed by chemical reduction of the B site metal cations to lower oxidation states, including the elemental state. When metal cations within the perovskite lattice structure are reduced, they tend to "swell" due to an increase in the atomic radius and thereby distort or destroy the crystal lattice structure.

Another reason the temperature is usually kept below about 400° C. is that thermal runaway usually occurs at temperatures below 400° C. Thermal runaway refers to the condition wherein there is virtually 100 percent conversion of the starting material and the major product is methane. Associated with thermal runaway is the formation of a "hot spot" in the catalyst bed where temperatures may exceed the temperature of the heating medium by as much as 100° C. or more.

The reactor can be heated and maintained at temperatures from about 200° C. to about 400° C. by a variety of methods, including a sandbath heater. The syn gas is fed into the reactor using any suitable means. Since all of the reaction products have boiling points lower than these temperatures, the reaction products will be gases. Consequently, the reaction product gases are conducted to a condenser where they are condensed and collected. Later, the reaction products can be separated and purified by distillation.

Typically, about 10 grams of a mixture of perovskite and silicon dioxide prepared as described above are placed in the reactor. The mixture can be placed on top of a bed of silicon dioxide, such as a one inch deep bed, which serves as an inert preheating zone. It is preferable to place a plug of glass wool at the exit of the reactor to prevent particles of the catalyst from being entrained by the reaction product gases.

The process of this invention can be employed to convert syn gas to lower oxygenated organic compounds including such commercially useful products as methanol, ethanol, acetaldehyde, acetic acid, esters of acetic acid, propanols, propionic acid, esters of propionic acid, butanols, pentanols, and hexanols. It can also be used where CO is a by-product to convert CO to less harmful compounds.

The invention is illustrated by the following examples.

EXAMPLE 1

65 grams (0.050 mole) of $La(NO_3)_3 \cdot 6H_2O$ and 14.45 grams (0.050 mole) of $Co(NO_3)_2 \cdot 6H_2O$ were dissolved in about one half liter of distilled water and the solution was placed in an addition funnel. 268 millimeters (0.75 mole) of 2.8 molar tetramethyl ammonium hydroxide in about one half liter of distilled water were placed in a two liter beaker equipped with a magnetic stirrer. The water solution containing the metal salts was added dropwise to the base solution over a period of about thirty minutes. The resulting precipitate of mixed hydroxides of $La(OH)_3$ and $Co(OH)_2$ was stirred for two to three hours and then suction filtered through a coarse Buchner funnel. The resulting filter cake was washed repeatedly with distilled water and sucked as dry as possible after each washing. The washings were continued until the pH of the wash water was in the range of about eight to about nine. The precipitate was dried in a vacuum oven maintained at 150° C. and about 350 millimeters Hg, absolute. Air was swept through the oven to promote evaporation of the water.

After drying, the resulting dry powder was ground with a mortar and pestle to a particle size of less than ten mesh. The material was then placed in an alumina crucible and heated in a calcining oven equipped with an air sweep for about 24 hours to convert the mixed metal hydroxides to $LaCoO_3$. After calcining, the sample was ground to a particle size of less than 50 mesh. The resulting $LaCoO_3$ powder was combined with about 100-200 mesh silicon dioxide powder at a 1:1 weight ratio and pressed into a tablet using a ram and die and a hydraulic press as described above. The resulting tablet was then crushed and sieved to about a 10-40 mesh powder.

The $LaCoO_3$ catalyst-silicon dioxide mixture was then placed in a U-tube reactor. The reactor was constructed of 316-stainless steel with openings at both ends. The catalyst bed section of the reactor was about 21 inches long with an outside diameter of one-half inch (inside diameter=three eights inch). The remainder of the reactor was made of one-fourth inch, 316-stainless steel tubing.

Before the catalyst-silicon dioxide mixture was added to the reactor, a one inch bed of silicon dioxide was placed in the bottom of the U-tube reactor to serve as an inert preheating zone. A plug of glass wool was placed in the exit of the reactor to prevent catalyst particles from being entrained by the product gases.

The reactor was heated by a sandbath heater equipped with a Barber Coleman programmable temperature controller. Individual Hastings automatic flow controllers were attached to the reactor to control the feeding of $H_2$, CO and $N_2$ gases into the reactor. The ratio of $H_2$ to CO to $N_2$ was 6:3:1 based upon volume. Since nitrogen was inert under the reaction conditions, it was used as an internal standard to correct for gas volume changes resulting from syn gas conversion.

After the catalyst was placed in the reactor, the reactor sandbath was heated to 150° C. and the feed gas flow rates and reactor pressure established. The gases were fed through their respective automatic flow controllers and combined into a single gas stream which was then fed through a static gas mixer to a diaphragm compressor and into the reactor. Reactor pressure was controlled at 970 pounds per square inch, gauge (psig) with a back pressure regulator. After establishing the feed rates and reactor pressure, the reactor temperature was raised from 150°–220° C. over a period of one hour and then held at 220° C. for five hours using the automatic temperature controller.

Using the reactor temperature controller, the reactor temperature was then raised in 20° C. increments to 320° C. where thermal runaway occurred. For each increment in temperature, one hour was allowed to raise the temperature from the previous level and stabilize the temperature at the new level. The temperature was then held at that level for five more hours before proceeding to next level. During the first three hours of each temperature level, triplicate analyses of the feed gases were obtained, and during the last three hours, triplicate analyses of the product stream were obtained. The results of triplicate analyses were then averaged.

Analyses were performed with a Hewlett Packard model 5880-A gas chromatograph equipped with a single oven, automatic sampling valves, appropriate stream switching valves, dual column trains, and dual detectors. One column train consisted of three columns with appropriate switching valves for analysis of permanent gases and lower organics. The other column was 7 feet by ⅛ inch (nickel) packed with Chromosorb-101 (80–120 mesh). Gas chromatograph analyses were performed on line, and products were identified by their retention times. When necessary, liquid products were condensed and analyzed off-line by gas chromatography-mass spectroscopy.

The results are shown in Table I.

for combined oxygenated organic compounds was observed.

The perovskites that were tested but did not show a selectivity of at least eight mol percent for combined lower oxygenated organic compounds in the temperature range of 200° C. to 400° C. were:
$LaMnO_3$, $LaMn_{0.5}Co_{0.5}O_3$, $La_{0.8}Ce_{0.2}CoO_3$, $La_{0.8}Sr_{0.2}CoO_3$, $LaCo_{0.5}Ru_{0.5}O_3$, $LaNi_{0.5}Ti_{0.5}O_3$, $NdFeO_3$, $NdCoO_3$, and crystalline $BaIrO_3$.

The above examples demonstrate that each perovskite differs in its selectivity for producing lower oxygenated organic compounds. The degree of selectivity is temperature dependent and there is an optimum temperature at which the greatest percent of lower oxygenated organic compounds as a percent of reaction products is obtained. The examples further demonstrate that only through experimentation can one determine if a particular perovskite has an appropriate selectivity for lower oxygenated organic compounds. (See Table I where for $LaCoO_3$, when it was tested at temperatures ranging from 220°–320° C., only at temperatures between 260° C. and 300° C. were selectivities for lower oxygenated organic compounds of eight mol percent or above observed).

TABLE I

CATALYTIC EVALUATION OF $LaCoO_3/SiO_2$-(1:1 ratio)
SUMMARY OF RESULTS

| $H_2:CO:N_2$ | PRES. PSIG | GHSV l/h | TEMP. °C. | CO CONV % | MEOH % | $C_2OX$ % | HIOX % | HC % | $CO_2$ % | OXY STY G/L.H | TOTAL STY G/L.H |
|---|---|---|---|---|---|---|---|---|---|---|---|
| 6:3:1 | 970 | 3944 | 220 | 0.56 | | | | 100 | | | 3.6 |
| 6:3:1 | 970 | 3944 | 240 | 1.8 | | | | 97.7 | 2.3 | | 12.5 |
| 6:3:1 | 970 | 3944 | 260 | 1.8 | 2.6 | 4.4 | 2.2 | 87.0 | 3.7 | 2.1 | 14.6 |
| 6:3:1 | 970 | 3944 | 280 | 2.3 | 12.5 | 10.0 | 10.6 | 62.4 | 4.4 | 9.4 | 21.5 |
| 6:3:1 | 970 | 3944 | 300 | 9.2 | 10.3 | 15.7 | 0.7 | 37.9 | 35.4 | 35.7 | 134.0 |
| 6:3:1 | 970 | 3944 | 320 | 100.0 | 3.7 | 3.3 | | 64.5 | 28.4 | 91.5 | 1120.0 |

EXAMPLE 2

Example 1 was repeated except that different perovskites were used instead of $LaCoO_3$ and some of the perovskite preparation and reaction conditions were different. Perovskite to silicon dioxide ratios of 1:1 were employed for the lanthanum and neodymium perovskites and 1:4 for the barium perovskites. Tetramethyl ammonium hydroxide was used as the precipitating agent for all the lanthanum and neodymium perovskites. Reaction pressures were in the range of about 970 to about 1030 psi. Gas hourly space velocities were in the range of about 2350 to about 4000 liters of reactant gases per liter of catalyst charge per hour. Gas volumes were corrected to 25° C. and one atmosphere of pressure. Catalyst volumes were determined for perovskite-silicon dioxide mixtures with particle sizes of about 10 to about 40 mesh.

Table II lists the appropriate starting materials for each perovskite catalyst that was tested and that showed carbon selectivities of at least eight mol percent for combined oxygenated organic compounds. The temperature of calcination is also shown in Table II. Table III summarizes the syn gas conversion results for catalysts that showed at least an eight mol percent carbon selectivity for combined oxygenated organic compounds. Table III contains gas hourly space velocities, carbon monoxide conversion, the products of the reaction for each catalyst, space time yields, and the temperatures at which eight mol percent or greater selectivity The ratio of gases is by volume.

PRES. PSIG. is reactor pressure and is measured in pounds per square inch, gauge.

GHSV is gas hourly space velocity and is measured as the volume of reactant gases (corrected to 25° C. and one atmosphere) fed to the reactor per hour divided by the volume of the catalyst (perovskite+silicone dioxide) charged to the reactor.

CO CONV % is the amount of CO converted expressed as a percent by weight of the starting amount of CO.

CO Selectivity, Percent is the selectivity for each product or group of products and is expressed as a mol percent i.e. the moles of carbon contained in each product or group of products is expressed as a percent of the total moles of carbon contained in the product stream excluding unreacted CO. The product abbreviations are the following:

MeOH=methanol; $C_2OX$=ethanol+acetaldehyde+acetic acid; HiOX=propanols, propionic acid, butanols, pentanols, and hexanols; HC=hydrocarbons from $C_1$ to $C_{10}$.

OXY STY is the space time yield of combined oxygenated organic compounds and is measured as the grams of combined oxygenated organic products produced per liter of catalyst charge per hour.

TOTAL STY is the space time yield of all carbon containing products and is measured as the grams of combined carbon containing products produced per liter of catalyst charge per hour.

TABLE II

PREPARATION OF PEROVSKITE CATALYSTS: REAGENTS AND CONDITIONS

| CATALYST | METAL PRECURSORS | CALCINATION TEMPERATURE °C. | ATMOSPHERE | TIME (DAYS) |
|---|---|---|---|---|
| $LaCoO_3$ | $La(NO_3)_3.6H_2O$<br>$Co(NO_3)_2.6H_2O$ | 700 | Air | 1.0 |
| $LaNiO_3$ | $La(NO_3)_3.6H_2O$<br>$Ni(NO_3)_2.6H_2O$ | 700 | Air | 1.0 |
| $LaFeO_3$ | $La(NO_3)_3.6H_2O$<br>$Fe(NO_3)_3.9H_2O$ | 700 | Air | 1.0 |
| $LaFe_{0.5}Co_{0.5}O_3$ | $La(NO_3)_3.6H_2O$<br>$Fe(NO_3)_3.9H_2O$<br>$Co(NO_3)_2.6H_2O$ | 900 | Air | 1.0 |
| $LaNi_{0.5}Co_{0.5}O_3$ | $La(NO_3)_3.6H_2O$<br>$Ni(NO_3)_2.6H_2O$<br>$Co(NO_3)_2.6H_2O$ | 800 | Air | 1.0 |
| $LaNi_{0.5}Fe_{0.5}O_3$ | $La(NO_3)_3.6H_2O$<br>$Ni(NO_3)_2.6H_2O$<br>$Fe(NO_3)_3.9H_2O$ | 700 | Air | 1.0 |
| $LaFe_{0.5}Ru_{0.5}O_3$ | $LaCl_3.6H_2O$<br>$FeCl_3.6H_2O$<br>$RuCl_3.6H_2O$ | 900 | Air | 1.0 |
| $LaNi_{0.5}Ru_{0.5}O_3$ | $LaCl_3.6H_2O$<br>$NiCl2.6H_2O$<br>$RuCl_3.6H_2O$ | 700 | Air | 1.0 |
| $LaMn_{0.5}Ni_{0.5}O_3$ | $La(NO_3)_3.6H_2O$<br>$Mn(NO_3)_2.xH_2O$<br>$Ni(NO_3)_2.6H_2O$ | 700 | Air | 1.0 |
| $LaMn_{0.5}Fe_{0.5}O_3$ | $La(NO_3)_3.6H_2O$<br>$Mn(NO_3)_2.x H_2O$<br>$Fe(NO_3)_3.9H_2O$ | 700 | Air | 1.0 |
| $LaFe_{0.5}Ti_{0.5}O_3$ | $LaCl_3.6H_2O$<br>$FeCl_3.6H_2O$<br>$TiCl_4$ | 700 | Air | 1.0 |
| $LaCu_{0.5}Ti_{0.5}O_3$ | $LaCl_3.6H_2O$<br>$CuCl_2$<br>$TiCl_4$ | 700 | Air | 1.0 |
| $LaCu_{0.5}Mn_{0.5}O_3$ | $La(NO_3)_3.6H_2O$<br>$Cu(NO_3)_2.6H_2O$<br>$Mn(NO_3)_2.xH_2O$ | 700 | Air | 1.0 |
| $BaRuO_3$, Amorphous | $K_2RuCl_6$<br>$BaCl_2$ | 350 | Oxygen | 1.0 |
| $BaRuO_3$, Crystalline | $K_2RuCl_6$<br>$BaCl_2$ | 1020 | Oxygen | 2.5 |
| $BaPtO_3$, Amorphous | $Na_2Pt(OH)_6$<br>$BaCl_2$ | 350 | Oxygen | 1.0 |
| $BaPtO_3$, Crystalline | $Na_2Pt(OH)_6$<br>$BaCl_2$ | 600 | Oxygen | 1.0 |
| $BaRhO_3$, Crystalline | $RhCl_3.3H_2O$<br>$BaCl_2$ | 700 | Oxygen | 1.0 |
| $BaRhO_3$, Amorphous | $RhCl_3.3H_2O$<br>$BaCl_2$ | 350 | Oxygen | 1.0 |
| $BaIrO_3$, Amorphous | $K_2IrCl_6$<br>$BaCl_2$ | 400 | Oxygen | 1.0 |
| $NdNiO_3$ | $Nd(NO_3)_3.5H_2O$<br>$Ni(NO_3)_2.6H_2O$ | 800 | Air | 1.0 |

TABLE III

CATALYTIC EVALUATION OF PEROVSKITES FOR SYN GAS CONVERSION: SUMMARY OF RESULTS

| CATALYST COMPOSITIONS | GHSV 1/HR | TEMP °C. | CO CONV % | CO SELECTIVITY, % | | | | | STY, G/L.HR | |
|---|---|---|---|---|---|---|---|---|---|---|
| | | | | MeOH | $C_2OX$ | HiOX | HC | $CO_2$ | OXY | TOTAL |
| $LaNiO_3$ | 2471 | 320 | 4.1 | 20.8 | 4.7 | 1.6 | 55.6 | 17.3 | 8.2 | 24.9 |
| | 2434 | 340 | 8.7 | 10.6 | 2.9 | 0.9 | 62.2 | 23.5 | 10.1 | 59.1 |
| $LaFeO_3$ | 3000 | 280 | 3.9 | 6.4 | 15.0 | 2.5 | 66.5 | 9.6 | 7.8 | 25.0 |
| | | 300 | 10.4 | 4.5 | 14.0 | 2.3 | 66.3 | 12.8 | 16.7 | 63.6 |
| | | 320 | 22.8 | 3.7 | 8.2 | 2.1 | 70.3 | 15.6 | 24.7<br>142.5 | |
| | 2990 | 300 | 9.8 | | 8.0 | 5.7 | 76.9 | 9.0 | 8.2 | 52.0 |
| | | 320 | 30.4 | 4.6 | 13.2 | 3.8 | 62.3 | 16.1 | 50.9<br>204.0 | |
| | | 340 | 22.1 | 4.9 | 12.6 | 2.2 | 67.0 | 13.1 | 35.6<br>144.2 | |
| | | 360 | 27.0 | 4.1 | 8.5 | 2.2 | 65.6 | 19.6 | 33.1<br>190.0 | |
| $LaNi_{0.5}Fe_{0.5}O_3$ | 3487 | 340 | 9.5 | 0.9 | 31.3 | | 54.6 | 13.1 | 33.1 | 55.1 |

TABLE III-continued
CATALYTIC EVALUATION OF PEROVSKITES FOR SYN GAS CONVERSION: SUMMARY OF RESULTS

| CATALYST COMPOSITIONS | GHSV l/HR | TEMP °C. | CO CONV % | CO SELECTIVITY, % | | | | | STY, G/L.HR | |
|---|---|---|---|---|---|---|---|---|---|---|
| | | | | MeOH | C$_2$OX | HiOX | HC | CO$_2$ | OXY | TOTAL |
| | | 360 | 15.2 | 0.6 | 16.0 | | 66.7 | 16.8 | 28.6 | |
| | | | | | | | | | 111.7 | |
| | | 380 | 26.4 | | 8.7 | | 73.3 | 17.9 | 26.1 | |
| | | | | | | | | | 212.8 | |
| LaMn$_{0.5}$Ni$_{0.5}$O$_3$ | 3504 | 320 | 2.6 | | 26.6 | | 61.5 | 11.9 | 6.5 | 15.8 |
| | | 340 | 4.5 | 0.8 | 15.6 | | 69.3 | 14.4 | 6.9 | 31.3 |
| | | 360 | 6.5 | 0.6 | 10.8 | | 71.5 | 17.1 | 6.9 | 48.8 |
| | | 380 | 7.5 | 0.1 | 9.2 | | 68.5 | 22.2 | 6.5 | 63.0 |
| LaNi$_{0.5}$Co$_{0.5}$O$_3$ | 3529 | 300 | 7.4 | 1.4 | 13.9 | 0.4 | 73.1 | 11.3 | 50.1 | |
| | | | | | | | | 11.6 | | |
| LaFe$_{0.5}$Co$_{0.5}$O$_3$ | 3529 | 320 | 13.6 | | 19.0 | | 73.5 | 7.5 | 28.4 | 80.0 |
| | | 340 | 30.2 | 0.5 | 8.1 | | 79.4 | 12.0 | 26.4 | 213.2 |
| LaMn$_{0.5}$Fe$_{0.5}$O$_3$ | 3769 | 340 | 10.4 | 5.3 | 4.6 | 4.0 | 69.5 | 16.7 | 18.6 | 115.0 |
| | | 360 | 15.9 | 3.9 | 3.7 | 2.0 | 69.4 | 20.9 | 18.6 | 170.0 |
| LaFe$_{0.5}$Ru$_{0.5}$O$_3$ | 2658 | 300 | 5.7 | | 12.6 | 0.9 | 81.3 | 5.2 | 5.5 | 26.1 |
| | | 320 | 11.0 | | 8.5 | 0.7 | 79.1 | 11.7 | 7.0 | 59.6 |
| | | 360 | 60.7 | 0.1 | 1.5 | 8.5 | 67.4 | 22.6 | 132.0 | |
| | | | | | | | | 14.7 | | |
| LaNi$_{0.5}$Ru$_{0.5}$O$_3$ | 3015 | 340 | 19.6 | 6.7 | 3.7 | 0.4 | 82.6 | 6.7 | 6.6 | 130.0 |
| LaFe$_{0.5}$Ti$_{0.5}$O$_3$ | 3189 | 340 | 11.4 | 6.9 | 10.1 | 1.3 | 60.2 | 21.5 | | 95.5 |
| | | 360 | 16.5 | 4.9 | 4.7 | 0.6 | 64.0 | 26.9 | 143.0 | |
| | | | | | | | | 15.9 | | |
| LaCu$_{0.5}$Ti$_{0.5}$O$_3$ | 3323 | 320 | 2.9 | 38.0 | | 0.9 | 28.7 | 32.4 | 35.6 | |
| | | | | | | | | 13.8 | | |
| | | 340 | 5.0 | 32.3 | | 1.6 | 32.6 | 33.6 | 20.7 | 60.6 |
| | | 360 | 7.6 | 24.1 | | 2.0 | 35.4 | 36.8 | 23.3 | 88.3 |
| | | 380 | 10.4 | 15.6 | | 1.7 | 45.6 | 37.1 | 20.9 | 116.0 |
| LaCu$_{0.5}$Mn$_{0.5}$O$_3$ | 3361 | 320 | 3.4 | 37.0 | | | 29.0 | 34.0 | 14.2 | 38.2 |
| | | 340 | 6.5 | 28.9 | | 0.6 | 36.3 | 34.2 | 21.2 | 69.4 |
| | | 360 | 12.4 | 20.5 | | 1.3 | 48.8 | 29.4 | 30.0 | 121.5 |
| | | 380 | 14.1 | 14.8 | | 1.5 | 42.2 | 41.5 | 24.8 | 151.9 |
| NdNiO$_3$ | 3561 | 280 | 7.0 | | 9.8 | | 90.2 | | 6.0 | 43.3 |
| BaRuO$_3$, Amorphous | 2381 | 300 | 9.6 | | 4.3 | 3.8 | 81.5 | 10.4 | 4.6 | 46.3 |
| BaRuO$_3$ Crystalline | 3564 | 260 | 6.6 | 1.5 | 12.1 | 0.6 | 66.6 | 19.2 | 7.5 | 49.2 |
| | | 280 | 13.4 | | 8.7 | 1.1 | 66.9 | 23.3 | 8.9 | 91.9 |
| BaRhO$_3$ Amorphous | 2556 | 240 | 1.1 | 54.3 | 2.4 | 0.9 | 27.5 | 14.9 | 6.9 | 10.3 |
| | | 260 | 2.5 | 36.6 | 8.4 | 1.5 | 29.8 | 23.6 | 11.7 | 24.8 |
| | | 280 | 6.7 | 22.6 | 10.2 | 3.1 | 38.8 | 25.4 | 22.2 | 60.6 |
| | | 300 | 16.7 | 13.4 | 10.3 | 3.2 | 44.3 | 28.9 | 39.2 | 147.0 |
| | | 320 | 6.3 | 6.1 | 3.6 | 2.4 | 71.0 | 16.8 | 6.1 | 41.2 |
| | | 340 | 21.8 | 2.4 | 4.5 | 4.4 | 67.2 | 21.5 | 16.7 | 142.0 |
| BaRhO$_3$ Crystalline | 2483 | 260 | 1.7 | 62.3 | 2.2 | 0.5 | 22.2 | 12.8 | 11.6 | 16.8 |
| | | 280 | 3.9 | 46.8 | 5.0 | 1.0 | 28.2 | 19.0 | 19.9 | 35.9 |
| | | 300 | 7.9 | 29.7 | 5.9 | 1.3 | 36.9 | 26.2 | 28.3 | 73.3 |
| | | 320 | 19.0 | 15.5 | 6.4 | 1.6 | 43.2 | 33.2 | 40.8 | 174.0 |
| | | 340 | 49.6 | 4.7 | 5.3 | 1.5 | 51.5 | 37.0 | 49.1 | 455.0 |
| BaIrO$_3$ Amorphous | 2576 | 280 | 2.9 | 29.3 | 7.7 | 2.2 | 43.1 | 17.6 | 10.8 | 24.1 |
| | | 300 | 8.7 | 20.4 | 5.8 | 2.1 | 51.0 | 20.6 | 23.1 | 71.4 |
| | | 320 | 21.4 | 17.1 | 5.1 | 1.4 | 47.6 | 28.7 | 43.7 | 173.0 |
| | | 340 | 22.0 | 8.8 | 6.2 | 1.0 | 61.2 | 22.8 | 30.7 | 162.0 |
| | | 360 | 34.0 | 5.1 | 3.0 | 0.9 | 61.4 | 29.5 | 25.6 | 260.0 |
| BaPtO$_3$ Amorphous | 2540 | 260 | 3.4 | 30.0 | 6.0 | 4.1 | 30.8 | 29.0 | 12.2 | 31.1 |
| | | 280 | 5.7 | 38.6 | 4.8 | 2.2 | 26.4 | 28.0 | 25.0 | 55.3 |
| | | 300 | 8.4 | 48.1 | 3.4 | 6.2 | 19.6 | 22.6 | 44.5 | 78.7 |
| | | 320 | 10.6 | 53.8 | 4.3 | 0.4 | 19.8 | 21.6 | 59.5 | 102.0 |
| | | 340 | 12.7 | 49.6 | 1.9 | 0.2 | 25.2 | 23.0 | 63.1 | 119.0 |
| | | 360 | 13.3 | 39.8 | 1.9 | 0.2 | 31.5 | 26.6 | 52.2 | 120.0 |
| | | 380 | 12.1 | 24.7 | 3.0 | 0.2 | 42.2 | 29.8 | 33.3 | 112.0 |
| BaPtO$_3$ Crystalline | 2860 | 300 | 1.5 | 47.8 | 0.4 | | 20.7 | 31.1 | 8.8 | 16.9 |
| | | 320 | 2.6 | 46.0 | 1.5 | | 24.2 | 28.4 | 14.6 | 16.3 |
| | | 340 | 4.4 | 49.1 | 1.2 | 0.2 | 23.6 | 25.9 | 25.5 | 23.5 |
| | | 360 | 6.7 | 43.8 | 8.1 | 0.3 | 24.2 | 23.2 | 38.7 | 34.7 |
| | | 380 | 6.5 | 37.1 | 1.8 | 0.3 | 32.0 | 38.9 | 30.6 | 45.5 |

The abbreviations in Table III are the same as those in Table I. Where only one GHSV value is listed for a particular catalyst it means that the GHSV value was constant. The reaction pressure was 1000 psig for all the catalysts except amorphous BaPtO$_3$ (970 psig) and crystalline BaRuO$_3$ (1030 psig).

We claim:

1. A process for synthesis gas conversion comprising reacting synthesis gas comprising hydrogen and carbon monoxide at a pressure in the range of 100 to 20,000 psig and at a temperature in the range of about 200° C. to about 400° C. in the presence of a perovskite catalyst such that the selectivity for lower oxygenated organic compounds containing one to six carbon atoms is at least about eight mol percent and wherein the perovskite catalyst is selected from the group consisting of (1) LaMO$_3$ where M=Co, Ni, Fe and mixtures thereof; (2) LaMn$_{0.5}$Ni$_{0.5}$O$_3$; (3) LaMn$_{0.5}$Fe$_{0.5}$O$_3$; (4) LaM$_{0.5}$Ru$_{0.5}$O$_3$ where M=Fe or Ni; (5) LaCu$_{0.5}$M$_{0.5}$O$_3$ where M=Ti or Mn; (6) LaFe$_{0.5}$Ti$_{0.5}$O$_3$; (7) amorphous or crystalline BaMO$_3$ where M=Ru, Rh, or Pt; (8) amorphous BaIrO$_3$; and (9) NdNiO$_3$.

2. A process for synthesis gas conversion comprising reacting synthesis gas comprising hydrogen and carbon monixide at a pressure in the range of about 970 to about 1030 psig and at a temperature in the range of about 200° C. to about 400° C. in the presence of a perovskite catalyst and at a gas hourly space velocity in the range of about 2350 to about 4000 such that the selectivity for lower oxygenated compounds containing one to six carbon atoms is at least about eight mol percent, and wherein the perovskite catalyst is selected from the group consisting of (1) LaMO$_3$ where M=Co, Ni, Fe and mixtures thereof; (2) LaMn$_{0.5}$Ni$_{0.5}$O$_3$; (3) LaMn$_{0.5}$Fe$_{0.5}$O$_3$; (4) LaM$_{0.5}$Ru$_{0.5}$O$_3$ where M=Fe or Ni; (5) LaCu$_{0.5}$M$_{0.5}$O$_3$ where M=Ti or Mn; (6) LaFe$_{0.5}$Ti$_{0.5}$O$_3$; (7) amorphous or crystalline BaMO$_3$ where M=Ru, Rh, or Pt; (8) amorphous BaIrO$_3$; and (9) NdNiO$_3$.

3. The process of claim 1 wherein the pressure is in the range of about 500 to about 10,000 psig.

4. The process of claim 1 wherein the pressure is in the range of about 970 to about 1030 psig.

5. The process of claim 1 wherein the gas hourly space velocity is in the range of about 1000 to about 100,000.

6. The process of claim 5 wherein the gas hourly space velocity is in the range of about 2000 to about 50,000.

7. The process of claim 6 wherein the gas hourly space velocity in the range of about 2350 to about 4000.

8. The process of claims 1 or 2 wherein the synthesis gas is comprised of about a 1:20 to about a 20:1 by volume ratio of hydrogen to carbon monoxide, respectively.

9. The process of claim 8 wherein the ratio is about 1:2 to about 5:1.

10. The process of claim 9 wherein the ratio is about 2:1.

11. The process of claims 1 or 2 wherein the perovskite catalyst is mixed with a binder prior to being employed in synthetic gas conversion.

12. The process of claims 1 or 2 wherein the binder is silicon dioxide.

13. The process of claim 12 wherein the perovskite and silicon dioxide are mixed together at a ratio of about 1:1 to about 1:5, respectively, based upon the total weight of the two materials, pressed into a tablet, and ground into a powder having a mesh in the range of about 50 to about 400 mesh.

14. The process of claim 13 wherein the ratio is about 1:1 or about 1:4.

15. The process of claim 13 wherein the mesh is in the range of about 100 to about 200.

16. The process of claims 1, 2, 3 or 4 wherein the perovskite is LaCoO$_3$ and the temperature is in the range of about 280° C. to about 300° C.

17. The process of claims 1, 2, 3 or 4 wherein the perovskite is LaNiO$_3$ and the temperature is in the range of about 320 C. to about 340° C.

18. The process of claims 1, 2, 3 or 4 wherein the perovskite is LaFeO$_3$ and the temperature is in the range of about 280° C. to about 360° C.

19. The process of claims 1, 2, 3 or 4 wherein the perovskite is La Ni$_{0.5}$Fe$_{0.5}$O$_3$ and the temperature is in the range of about 340° C. to about 380° C.

20. The process of claims 1, 2, 3 or 4 wherein the perovskite is La Ni$_{0.5}$ Co$_{0.5}$ O$_3$ and the temperature is about 300° C.

21. The process of claims 1, 2, 3 or 4 wherein the perovskite is La Fe$_{0.5}$ Co$_{0.5}$ O$_3$ and the temperature is in the range of about 320° C. to about 340° C.

22. The process of claims 1, 2, 3 or 4 wherein the perovskite is La Mn$_{0.5}$ Ni$_{0.5}$ O$_3$ and the temperature is in the range of about 320° C. to about 380° C.

23. The process of claims 1, 2, 3 or 4 wherein the perovskite is LaMn$_{0.5}$Fe$_{0.5}$O$_3$ and the temperature is in the range of about 340° C. to about 360° C.

24. The process of claims 1, 2, 3 or 4 wherein the perovskite is La Fe$_{0.5}$ Ru$_{0.5}$ O$_3$, and the temperature is in the range of about 300° C. to about 320° C. or is about 360° C.

25. The process of claims 1, 2, 3 or 4 wherein the perovskite is La Fe$_{0.5}$ Ti$_{0.5}$ O$_3$, and the temperature is in the range of about 340° C. to about 360° C.

26. The process of claims 1, 2, 3 or 4 wherein the perovskite is amorphous BaRuO$_3$ and the temperature is about 300° C.

27. The process of claims 1, 2, 3 or 4 wherein the perovskite is crystalline BaRuO$_3$ and the temperature is in the range of about 260° C. to about 280° C.

28. The process of claims 1, 2, 3 or 4 wherein the perovskite is amorphous BaPtO$_3$ and the temperature is about 260° C. to about 380° C.

29. The process of claims 1, 2, 3 or 4 wherein the perovskite is crystalline BaPtO$_3$ and the temperature is in the range of about 300° C. to about 380° C.

30. The process of claims 1, 2, 3 or 4 wherein the perovskite is amorphous BaRhO$_3$ and the temperature is in the range of about 240° C. to about 340° C.

31. The process of claims 1, 2, 3, or 4 wherein the perovskite is crystalline BaRhO$_3$ and the temperature is in the range of about 260° C. to about 340° C.

32. The process of claims 1, 2, 3 or 4 wherein the perovskite is amorphous BaIrO$_3$ and the temperature is in the range of about 280° C. to about 360° C.

33. The process of claims 1, 2, 3 or 4 wherein the perovskite is NdNiO$_3$ and the temperature is about 280° C.

34. The process of claims 1, 2, 3, or 4 wherein the perovskite is LaCu$_{0.5}$Ti$_{0.5}$O$_3$, and the temperature is in the range of about 320° C. to about 380° C.

35. The process of claims 1, 2, 3 or 4 wherein the perovskite is LaCu$_{0.5}$Mn$_{0.5}$O$_3$, and the temperature is in the range of about 320° C. to about 380° C.

36. The process of claims 1, 2, 3 or 4 wherein the perovskite is LaNi$_{0.5}$Ru$_{0.5}$O$_3$, and the temperature is about 340° C.

* * * * *